(12) United States Patent
Walther et al.

(10) Patent No.: US 9,375,435 B2
(45) Date of Patent: Jun. 28, 2016

(54) USE OF A DNA EXPRESSION CONSTRUCT

(75) Inventors: Wolfgang Walther, Pankethal (DE); Peter M. Schlag, Berlin (DE); Dennis Kobelt, Berlin (DE); Manuel Schmidt, Berlin (DE)

(73) Assignees: MOLOGEN AG, Berlin (DE); MAX-DELBRUCK-CENTRUM FUR MOLEKULARE MEDIZIN (MDC) BERLIN-BUCH, Berlin (DE)

( * ) Notice: Subject to any disclaimer, the term of this patent is extended or adjusted under 35 U.S.C. 154(b) by 0 days.

(21) Appl. No.: 13/820,888

(22) PCT Filed: Sep. 8, 2011

(86) PCT No.: PCT/EP2011/065546
§ 371 (c)(1),
(2), (4) Date: Jun. 17, 2013

(87) PCT Pub. No.: WO2012/032114
PCT Pub. Date: Mar. 15, 2012

(65) Prior Publication Data
US 2013/0273084 A1    Oct. 17, 2013

(30) Foreign Application Priority Data
Sep. 8, 2010    (GB) .................................. 1014907.8

(51) Int. Cl.
| | | |
|---|---|---|
| A61K 48/00 | (2006.01) | |
| A61K 31/547 | (2006.01) | |
| C12N 15/85 | (2006.01) | |
| A61K 38/19 | (2006.01) | |
| A61K 38/18 | (2006.01) | |
| A61P 35/00 | (2006.01) | |
| C12P 21/02 | (2006.01) | |
| C12P 21/04 | (2006.01) | |
| A61K 39/00 | (2006.01) | |

(52) U.S. Cl.
CPC ............. *A61K 31/547* (2013.01); *A61K 38/191* (2013.01); *A61K 48/005* (2013.01); *A61K 48/0066* (2013.01); *C12N 15/85* (2013.01); *A61K 2039/53* (2013.01); *C12N 2800/24* (2013.01)

(58) Field of Classification Search
None
See application file for complete search history.

(56) References Cited

U.S. PATENT DOCUMENTS

| 6,451,593 B1 | 9/2002 | Wittig et al. | |
|---|---|---|---|
| 7,635,468 B2 * | 12/2009 | Dobric et al. | ............. 424/93.21 |
| 2003/0125279 A1 * | 7/2003 | Junghans et al. | ................ 514/44 |
| 2009/0082295 A1 * | 3/2009 | Jungnelius et al. | ............. 514/44 |
| 2010/0297189 A1 * | 11/2010 | Dobric et al. | ............. 424/277.1 |

OTHER PUBLICATIONS

Walther et al., "Improved transfer efficiency and transgene expression in vitro and in vivo using the minimalistic nonviral MIDGE expression system" 50 Proceedings of the American Association for Cancer Research 915 (2009).*
Licht et al., "Modulation of vindesine and doxorubicin resistance in multidrug-resistant pleural mesothelioma cells by tumor necrosis factor-alpha" 1 Cytokines and Molecular Therapy 123-132 (1995).*
Endmann, A. et al., "Immune response induced by linear DNA vector: Influence of dose, formulation and route of injection," Vaccine, 2010, vol. 28, pp. 3642-3649.
International Search Report for PCT/EP2011/065546, Date of the actual completion of the international search: Dec. 6, 2011, Date of mailing of the international search: Dec. 23, 2011.
Leutenegger, C. M. et al., "Immunization of Cats against Feline Immunodeficiency Virus (FIV) Infection by Using Minimalistic Immunogenic Defined Gene Expression Vector Vaccines Expressing FIV gp140 Alone or with Feline Interleukin-12 (IL-12), IL-16, or a CpG Motif," Journal of Virology, Nov. 2000, pp. 10447-10457.
Ren, S. et al., "Low-volume jet injection for intradermal immunization in rabbits," BMC Biotechnology, 2002, vol. 2.
Schakowski, F. et al., "A novel minimal-size vector (MIDGE) Improves transgene expression in colon carcinoma cells avoids transfection of undesired DNA," Molecular Therapy, May 2001, vol. 3, No. 5, pp. 793-800.
Stein, U. et al., "Complete in Vivo Reversal of the Multidrug Resistance phenotype by jet-injection of anti-MDR1 Short Hairpin RNA-encoding plasmid DNA," Molecular Therapy, Jan. 2008, vol. 16, No. 1, pp. 178-186.
Walther, W. et al., "Low-volume jet injection for efficient nonviral in vivo gene transfer," Molecular Biotechnology, 2004, vol. 28, pp. 121-128.
Gitler et al. "Preclinical models for defining efficacy of drug combinations: mapping the road to the clinic." Molecular Cancer Therapeutics, 2009.
Zanta et al."Gene delivery: A single nuclear localization signal peptide is sufficient to carry DNA to the cell nucleus," PNAS, USA 96(1): 91-96, 1999.
Mayer et al. "Ratiometric dosing of anticancer drug combinations: Controlling drug ratios after systemic administration regulates therapeutic activity in tumor-bearing mice." Molecular Cancer Therapies Jul. 2006 5:1854-1863, 2009.
Wilkinson et al. "Surprise phase III failure for ZD1839." Lancet Oncology, 3, 583, 2002.

(Continued)

*Primary Examiner* — Nancy J Leith
(74) *Attorney, Agent, or Firm* — Millen, White, Zelano, Branigan, P.C.

(57) ABSTRACT

The present invention relates to the use of a DNA expression construct comprising a dumbbell-shaped circular strand of deoxyribonucleic acids and provides such a construct with a double-stranded stem and single-stranded loops located at both ends of the stem, wherein the stem comprises complementary deoxyribonucleic acids of the circular strand with a promotor sequence, a coding sequence and a termination signal to be administered by jet injection for the treatment of cancer.

7 Claims, 4 Drawing Sheets

(56) References Cited

OTHER PUBLICATIONS

European Office Action related to EP Application No. 11 767 194.1; dated Jun. 8, 2015.

Murugesan et al. "Combination of human tumor necrosis factor-alpha (hTNF-alpha) gene delivery with gemcitabine is effective in models of pancreatic cancer." Cancer Gene Ther. 16(11):841-7, Nov. 2009; Epub May 15, 2009.

* cited by examiner

USE OF A DNA EXPRESSION CONSTRUCT

FIELD OF THE INVENTION

The present invention relates to the use of a DNA expression construct comprising a dumbbell-shaped circular strand of deoxyribonucleic acids.

BACKGROUND OF THE INVENTION

Several DNA constructs or vectors, which are suitable for the expression of proteins, which are encoded by sequences within such a DNA construct, are known in the state of the art. Depending on the organism or cell type into which an expression construct should be introduced they are designated as eukaryotic or prokaryotic expression constructs. The term "plasmid" is commonly related to circular expression constructs comprising a covalently closed circular DNA double-strand. Plasmids usually contain further sequences in addition to the ones, which should be expressed, like marker genes for their specific selection and in some cases sequences for their episomal replication in a target cell.

A structurally different expression construct is described in the EP 0 941 318. This document discloses a dumbbell-shaped linear, covalently closed DNA construct with partially single stranded loops at both ends. Such a construct causes after transfection significantly increased levels of protein expression, depending on the method for introducing the DNA construct into the cell.

The EP 0 941 318 discloses further that it is advantageously with regard to the protein expression to apply such a dumbbell-shaped DNA constructs via ballistic transfer. Although the expression level increases, it is laborious to link the DNA by means of absorption, covalently or ionic binding to the micro projectiles which are used for the ballistic transfer.

Jet injectors, which are appropriate for DNA transfer into a cell, are known in the state of the art, e.g. for the application of vaccines. Such a jet injector is usually a medical device with an injecting syringe, which uses a high-pressure narrow jet for the injection of liquids. The difference to usually used hypodermic needles to penetrate the epidermis is that a jet injector reduces the pain associated with the corresponding injection. Commonly, a jet injector is powered by compressed air or gas, either by a pressure hose from a large cylinder or from a built in gas cartridge or small cylinder. Basically, jet injectors are used as alternatives to needle syringes.

BRIEF SUMMARY OF THE INVENTION

It is an objective of the present invention to provide an alternative use of a dumbbell-shaped DNA expression construct for the transfer into cells.

The present disclosure provides the use of a dumbbell-shaped linear, covalently closed DNA construct with a double-stranded stem and single-stranded loops located at both ends of the stem, wherein the stem of complementary deoxyribonucleic acids of a circular DNA strand comprises a promotor sequence, a coding sequence and a termination signal to be administered by jet injection for the treatment of cancer.

It is intended that the promotor sequence is operable in eukaryotic cells and human beings. It might be advantageous to adapt the used promotor to the tissue or the origin of the respective tissue, in order to optimize the expression rate after transfer into the cell or nucleus, respectively.

The DNA constructs can be used to encode immunomodulating agents and/or cell surface marker. The term "immunomodulator" comprises stimulators and suppressors of the immune system. The term "modulation of the immune system" is used synonymously with "activation of the immune system" either in the meaning of intensifying or suppressing an immune response.

The immunomodulating agents shall be selected from the group comprising antibodies, hormones, cytokines or other biologically active substances. The term "biologically active" comprises all substances, which cause an effect after their application or transfer into cells or tissues, wherein it does not matter whether the respective substance is synthetically produced or of biological origin, which includes genetically based methods of manufacture.

The use according to the disclosure comprises a DNA construct encoding transmitter or messenger of the immune system like cytokines, which are selected from the group comprising TNF-α, Interleukin-7, granulocyte-macrophage colony stimulating factor, CD40L/CD154 and B7.1/CD80. Besides the mentioned transmitter any other molecule mediating an immunological signal is within the scope of the present invention.

The use according to the disclosure covers also a DNA construct that is administered simultaneously or subsequently with a chemotherapeutic, wherein a simultaneous administration includes the option that one compound is released with a time-delay due to a corresponding formulation or coupling to adequate compounds.

The use according to the disclosure refers to chemotherapeutics selected from the group comprising antibodies, alkylating agents, platinum analoga, intercalating agents, antibiotics, mitosis suppresses, taxanes, topoisomerases suppressors, anti-metabolites and/or L-asparaginase, hydroxycarbamide, mitotanes and/or amanitines.

The mitosis suppressor vindesine showed very good results in combination with a dumbbell-shaped DNA expression construct encoding TNF-α.

It is further intended that the DNA construct is provided as pharmaceutically applicable composition, especially a vaccine.

The use according to the disclosure intends further the co-administration of a non-coding, immunosmodulatory DNA sequence by jet injection. Again, this additional compound can be administered simultaneously or subsequently and even in the case of simultaneous administration a time-delayed release can be intended.

It is intended that the DNA sequence of a non-coding DNA sequence comprises at least one sequence motif $N^1N^2CGN^3N^4$, wherein $N^1N^2$ is an element taken from the group of GT, GG, GA, AT or AA, and $N^3N^4$ is an element taken from the group of CT or TT, and C is desoxycytosine, G is desoxyguanosine, A is desoxyadenosine and T is desoxythymidinethe.

In case that the non-coding is an open-chained oligodeoxynecleotide suitable means for protection of the ends against nucleases are within the scope of the invention.

The non-coding immunomodulatory DNA can be dumbbell-shaped and comprise a covalently closed circular DNA single strand, which is partly double-stranded forming a double-stranded stem and single stranded loops at both ends of the stem.

DETAILED DESCRIPTION OF THE INVENTION

The present disclosure provides a new and inventive use of a DNA construct, which shall be administered by a jet injector into cells. On one hand the DNA may be injected directly into tissues like tumours, muscles or connective tissue. On the other hand the use according to the disclosure may be performed with cell cultures. Thus, the use is appropriate for in vivo an in vitro use.

The scope of the disclosure covers not only dumbbell-shaped expression constructs, but also circular double-stranded DNA expression constructs. Such an expression construct might encode TNF-α and should be applied together with a chemotherapeutic like vindesine.

The term "cancer" comprises cancerous diseases or a tumor being treated or prevented that is selected from the group comprising mammary carcinomas, melanoma, skin neoplasms, gastrointestinal tumors, including colon carcinomas, stomach carcinomas, pancreas carcinomas, colon cancer, small intestine cancer, ovarial carcinomas, cervical carcinomas, lung cancer, prostate cancer, kidney cell carcinomas and/or liver metastases.

The pharmaceutical shall be suitable for injection, especially jet injection, including sterile aqueous solutions or dispersions and sterile powders for the extemporaneous preparation of sterile injectable solutions or dispersions. In all cases the pharmaceutical shall be provided as sterile fluid in an extent that easy syringability or jet injection is possible. It has to be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferred to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts (formed with the free amino groups of the protein) and are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, Solutions will be administered in a manner compatible with the dosage formulation and in such amount as is therapeutically effective. The formulations are easily administered in a variety of dosage forms such as injectable Solutions, drug-release capsules, and the like.

As used herein, "carrier" includes any and all solvents, dispersion media, vehicles, coatings, diluents, antibacterial and antifungal agents, isotonic and absorption delaying agents, buffers, carrier Solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The term "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

BRIEF DESCRIPTION OF THE FIGURES

The disclosure will be illustrated by figures and examples without being limited to them. It shows.

DETAILED DESCRIPTION OF THE FIGURE

FIG. 1 shows the dose dependency of the protein expression and the presence of transferred DNA from the respective dose applied to the tumour. The transferred dumbbell-shaped DNA construct encoded TNF-α. Three different methods were applied to demonstrate the expression of TNF-α or the presence of the transferred DNA in melanomas, which are malignant tumours of melanocytes.

Figure 1A:
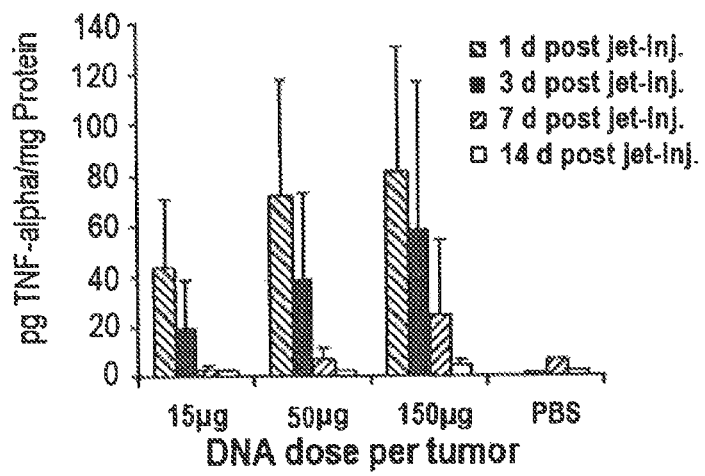
FIGS. 1A-1C show the dose dependency of dumbbell-shaped DNA jet injected into melanomas. A) TN F-E LISA results. B) Amount of transfected DNA construct (ng) per tumor. C) Immunofluorescence determination of TNF-α in tumors.

FIG. 1A shows the results of a TNF-ELISA with the applied DNA dose depicted on the x-axis (µg) in relation to the amount of TNF-α (pg) per amount of total protein (mg) on the y-axis for days one, three, seven and 14 after jet injection of the DNA.

It is obvious that the level of protein expression after jet injection depends on the DNA dose per tumour. For each time point after jet injection the protein expression has the highest level for 150 µg DNA. The strongest DNA expression can be observed one day after jet injection of 150 µg DNA and decreases for each further time point measured. On the right side of FIG. 1A PBS without any DNA is shown as negative control.

Figure 1B:
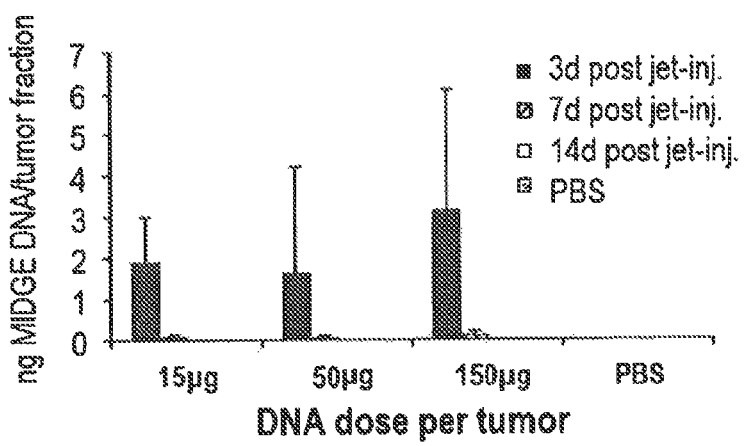

FIG. 1B shows the amount of transfected DNA construct (ng) per tumour fraction on the y-axis for different DNA doses for days three, seven and 14 after jet injection of the DNA. The DNA of the transfected dumbbell-shaped DNA construct was amplified by PCR and PBS was used as negative control, which is depicted on the right side of the x-axis.

The results of the DNA amplification coincide with the results of the protein determination in FIG. 1A. The highest level of DNA could be amplified three days after jet injection and a minimal amount of DNA could be determined seven days after jet injection.

Although the DNA dose of 50 µg per tumour results in less DNA expression than with 15 µg DNA, the error bar shows that the average DNA expression with 50 µg DNA was higher than with 15 µg. In total, the highest DNA dose of 150 µg per tumour resulted in the highest amount of transferred DNA, which was amplifiable by PCR.

Figure 1C:
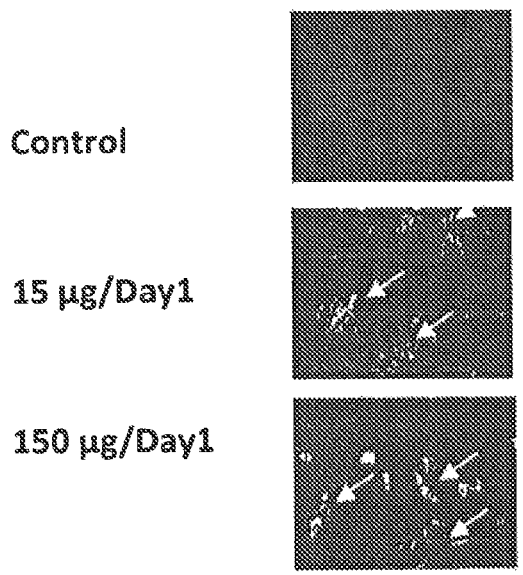

FIG. 1C shows an immunofluorescence for the determination of TNF-α expression in tumours. The arrows in the figures are depicting cells expressing TNF-α. It is obvious that the transfer of 15 µg and 150 µg results one day after jet injection in a clearly detectable expression of TNF-α. The picture on top shows the negative control.

Figure 2A:
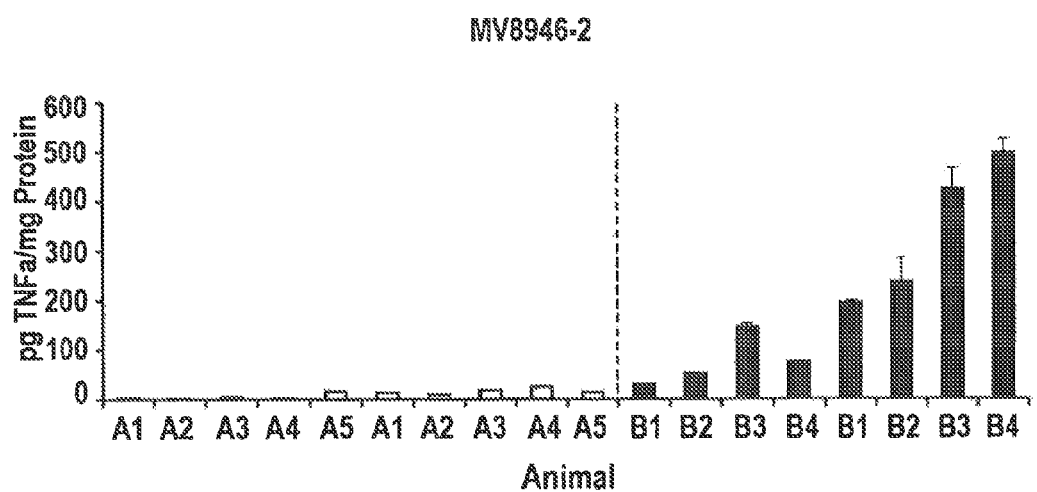
FIGS. 2A-B show in vivo expression efficiency in tumors comparing dumbbell-shaped DNA with circular double-stranded plasmids. A) TNF-α (pg) per mass of total protein (mg). B) Average amount of TNF-α per total protein mass.

FIG. 2 shows the in vivo expression efficiency in tumours comparing dumbbell-shaped DNA with circular closed double-stranded DNA. Both DNA expression constructs encode TNF-α. In FIGS. 2A and B the results for the plasmid DNA—double-stranded circular DNA—are depicted on the left side (open bars) in comparison to the results of the dumbbell-shaped DNA construct on each right side (black bars). Equimolar amounts of the respective DNA construct were applied.

Five different animals for the plasmid transfer and four different animals for the dumbbell-shaped DNA were used for the experiments and the weight of the tumours together with the mass of TNF (pg) per mass tumour (g) is indicated in the following table.

TABLE 1

| Animal # | Tumour weight | pgTNF/g tumour |
|---|---|---|
| 1 | 0.6 g | 7.005 |
| 2 | 1.25 g | 12.189 |
| 3 | 1.27 g | 6.567 |
| 4 | 0.62 g | 5.656 |
| 5 | 0.5 g | 6.898 |

FIG. 2A shows the amount of TNF-α (pg) per mass of total protein (mg). It is obvious that the use of plasmid DNA did not result in a measurable amount of expressed TNF-α (left side), wherein the use of the dumbbell-shaped DNA construct resulted in a clearly detectable amount of expressed TNF-α (right side).

Figure 2B:
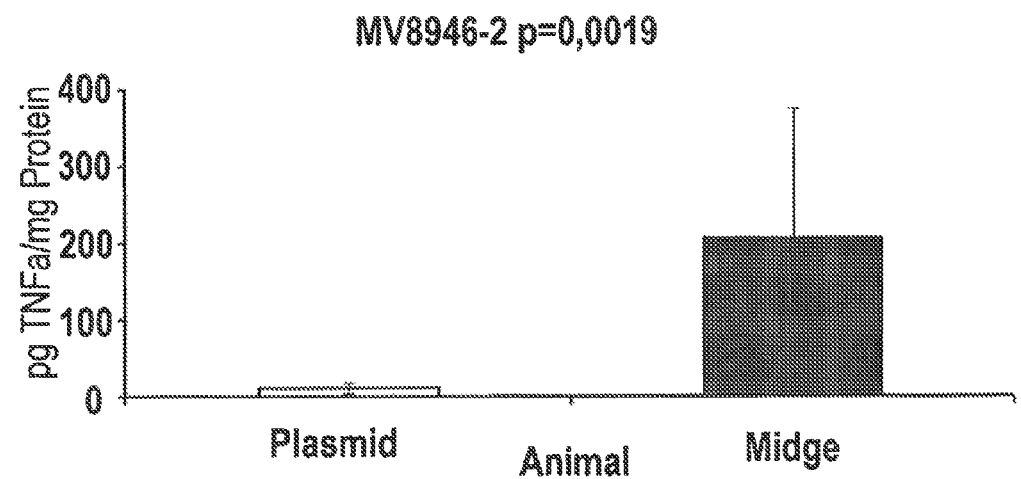

As it can be taken from FIG. 2B the average amount of TNF-α per total protein mass is about 200 fold more using the dumbbell-shaped DNA construct instead of plasmid DNA. The differences between the expression efficiencies for plasmid DNA versus dumbbell-shaped DNA are absolutely surprising and could not be expected, even when taking into account that jet injection might result in a better transfer of DNA constructs. Although the plasmid DNA was transferred by jet injection, it is nearly no TNF-α expression detectable, whereas the dumbbell-shaped DNA caused a considerable amount of expressed TNF-α.

In further experiments the effect of TNF-α expression on cell vitality and tumour volume was investigated. FIG. 3 shows the results of a gene transfer using a dumbbell-shaped DNA construct encoding TNF-α in combination with the chemotherapeutic vindesine (black bars) in comparison to the use of vindesine alone (open bars).

Figure 3A:
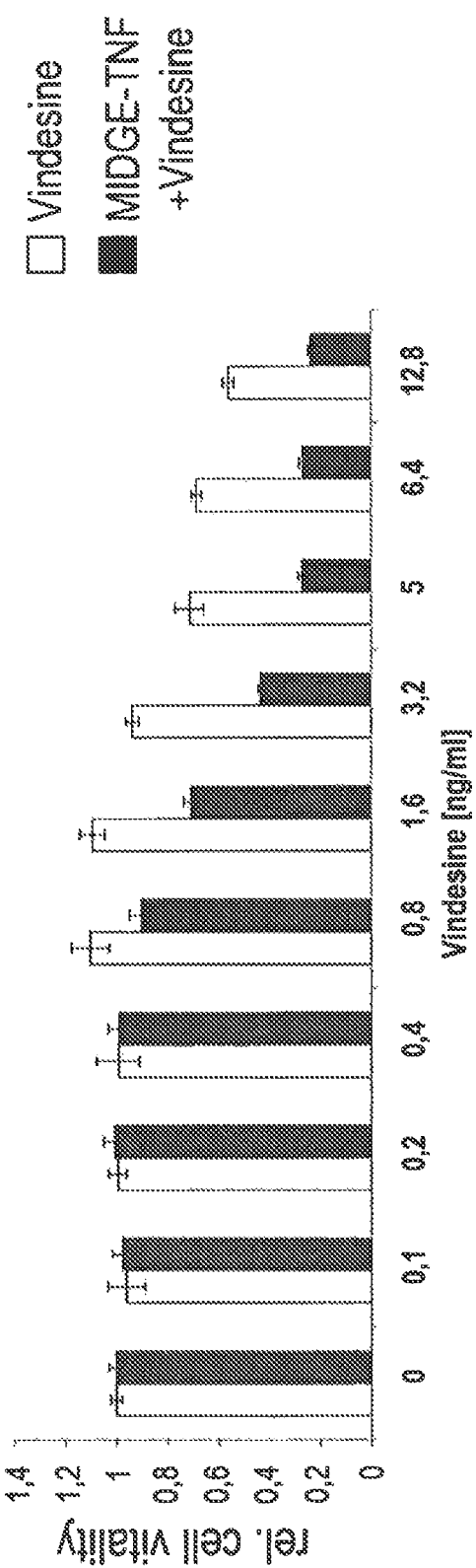
FIGS. 3A-3B show gene transfer using dumbbell-shaped DNA alone or in combination with vindesine. A) In vitro chemo-sensitization assay results. B) Chemo-sensitization of A375 melanoma xenotransplanted tumors.

FIG. 3A shows the results of an in vitro chemo-sensitization assay of A375 melanoma cells after the transfer of vindesine alone and in combination with a dumbbell-shaped DNA construct encoding TNF-α. It is clearly visible that the use of vindesine alone decreases cell vitality. This effect can be amplified by using a combination of vindesine with the dumbbell-shaped DNA construct encoding TNF-α. Using vindesine alone in a concentration of 12.8 µg per ml results in a relative cell vitality of 0.6 in comparison to 0.2 when using in parallel the dumbbell-shaped DNA construct encoding TNF-α. The degree of amplification of the effect is surprising and could not be traced back to the addition of the effect of the TNF-α encoding DNA construct and vindesine, respectively, as can be taken from FIG. 3B.

Figure 3B:
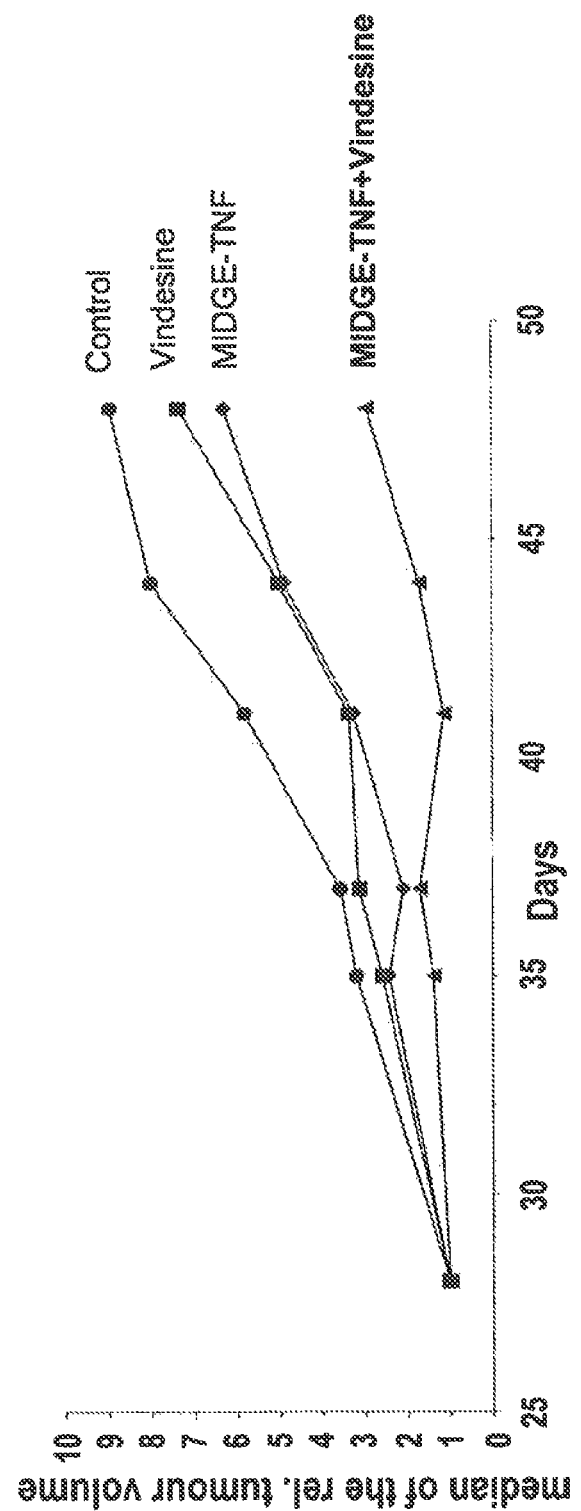

FIG. 3B shows the chemo-sensitization of A375 melanoma xenotransplanted-tumours by the gene transfer of the dumbbell-shaped DNA construct encoding TNF-α (MIDGE-TNF), vindesine and the combination of MIDGE-TNF with vindesine. The intratumoral jet injection was performed using twice 150 µg of the dumbbell-shaped DNA construct and where indicated additionally twice 0.5 mg/kg tumour vindesine.

On the y-axis is the median of the relative tumour volume shown for the indicated days after transfer (x-axis). The transfer of vindesine and MIDGE-TNF, respectively, reduces the average tumour volume, but the combination of vindesine and MIDGE-TNF has a clear synergistic effect, which is far beyond the simple addition of the effects when using the compounds alone. This result could not be expected and strengthens the hypothesis that the cell vitality (FIG. 3A) is also decreased by a synergistic effect when vindesine is applied by jet injection in combination with the TNF-α encoding dumbbell-shaped construct.

The figures show that a dumbbell-shaped DNA construct, which is applied by jet injection, leads to a multiple expression of encoded protein in comparison to jet injected plasmid DNA. The use of the dumbbell-shaped DNA construct in combination with a chemotherapeutic—like vindesine—has a synergistic effect on the tumour cell vitality and the tumour volume. Both effects could not be expected because they are much stronger than simply adding the effects of the compounds alone.

In general these results show that the use of a dumbbell-shaped DNA construct encoding for immunomodulators, namely immunostimulators or immunosuppressors, in combination with a chemotherapeutic and applying the DNA by jet injection is advantageously for the treatment of cancer or any other disease, which is related to uncontrolled cell growth.

We claim:

1. A method for the treatment of melanoma comprising administering to an animal in need thereof, a therapeutically effective amount of vindesine, and by jet injection, a dumbbell-shaped linear, covalently closed circular DNA expression construct with a double-stranded stem and single-stranded loops located at both ends of the stem, wherein the stem of complementary deoxyribonucleic acids of the circular DNA strand comprises a promotor sequence, a coding sequence which encodes tumor necrosis factor-α (TNF-α) and a termination signal.

2. The method of claim 1, wherein the promotor sequence is operable in eukaryotic cells and human beings.

3. The method of claim 1, wherein the DNA expression construct encoding TNF-α is administered simultaneously with or subsequently to the vindesine, wherein when the DNA construct is administered subsequently to the vindesine, the vindesine is still biologically active in the animal.

4. The method of claim 1, wherein the DNA construct is provided as a pharmaceutically applicable composition together with a carrier.

5. The method of claim 4, wherein the pharmaceutically applicable composition is a vaccine.

6. The method of claim 1, wherein the animal is a human subject.

7. The method of claim 1, wherein the melanoma is not resistant to vindesine.

* * * * *